US007569344B2

(12) United States Patent
Light et al.

(10) Patent No.: US 7,569,344 B2
(45) Date of Patent: Aug. 4, 2009

(54) DETECTION OF HUMAN PAPILLOMA VIRUS IN PAPANICOLAOU (PAP) SMEARS

(75) Inventors: Elizabeth S. Light, Gaithersburg, MD (US); Gerard J. Nuovo, Westerville, OH (US)

(73) Assignee: Ventana Medical Systems, Inc., Tuscon, AZ (US)

( * ) Notice: Subject to any disclaimer, the term of this patent is extended or adjusted under 35 U.S.C. 154(b) by 604 days.

(21) Appl. No.: 10/646,633

(22) Filed: Aug. 22, 2003

(65) Prior Publication Data

US 2005/0014133 A1 Jan. 20, 2005

Related U.S. Application Data

(63) Continuation-in-part of application No. 09/582,492, filed as application No. PCT/US99/25109 on Oct. 26, 1999.

(60) Provisional application No. 60/105,657, filed on Oct. 26, 1998.

(51) Int. Cl.
C12Q 1/68 (2006.01)
C12P 19/34 (2006.01)
C07H 21/04 (2006.01)

(52) U.S. Cl. ............... 435/6; 435/91.2; 435/91.1; 536/23.1; 536/24.32; 536/24.3

(58) Field of Classification Search ............ None
See application file for complete search history.

(56) References Cited

U.S. PATENT DOCUMENTS

| | | | |
|---|---|---|---|
| 4,820,530 A | 4/1989 | Moran et al. | |
| 4,849,311 A | 7/1989 | Itoh et al. | |
| 4,849,332 A | 7/1989 | Lorincz | |
| 4,849,334 A | 7/1989 | Lorincz | |
| 4,908,306 A | 3/1990 | Lorincz | |
| 4,983,728 A | 1/1991 | Herzog et al. | |
| 5,057,411 A | 10/1991 | Lancaster et al. | |
| 5,283,171 A | 2/1994 | Manos et al. | |
| 5,411,847 A | 5/1995 | Leppard et al. | |
| 5,484,699 A | 1/1996 | Bouma et al. | |
| 5,501,947 A | 3/1996 | Emery et al. | |
| 5,527,898 A | 6/1996 | Bauer et al. | |
| 5,538,871 A | 7/1996 | Nuovo et al. | |
| 5,554,538 A | 9/1996 | Cole et al. | |
| 5,639,871 A * | 6/1997 | Bauer et al. ........... 536/24.31 | |
| 5,643,715 A | 7/1997 | Lancaster | |
| 5,656,423 A | 8/1997 | Orth et al. | |
| 5,679,509 A | 10/1997 | Wheeler et al. | |
| 5,712,092 A | 1/1998 | Orth et al. | |
| 5,783,412 A | 7/1998 | Morris et al. | |
| 5,952,487 A | 9/1999 | Philipp et al. | |
| 5,981,173 A | 11/1999 | Orth et al. | |
| 6,855,552 B2 | 2/2005 | Towne et al. | |
| 6,933,117 B2 | 8/2005 | Wolf et al. | |

FOREIGN PATENT DOCUMENTS

EP 0477972 9/1996

OTHER PUBLICATIONS

Cox et al. (American Journal of Obstet. Gynecol. Mar. 1995, pp. 946-954).*
Nuovo et al. (The Journal of Histotechnology, vol. 18, No. 2, Jun. 1995).*
Nuovo et al. (Jun. 1998 Diagnostic Molecular Pathology 7(3): 158-163).*
Medical FAQS on the Natural History of HPV, American Society for Colposcopy and Cervical Pathology. copyright 2001-2007. printed pp. 1-9. printed Jan. 8, 2007 from http://cme.asccp.org/faq/histHPV.cfm.*
Togawa et al., Human papillomavurus-16 and -18 replication in esophagus squamous cancer cell line squamous cancer does not lines does not require heterologous E1 and E2 proteins., J. Med. Virol. 45:435-38 (1995).
Southern et al., "Basal cell tetrasomy in low-grade cervical squamous intraepithelial lesions infected with high-risk human papillomaviruses." Cancer Res., 57:4210-13 (1997).
Gravitt et al, "Genotyping of 27 human papilimavirus types by using L1 consensus PCR products by a singl-hybridization, reverse line blot detection method." J. Clin. Microbiol. 36:3020-27 (1998).
Jacobs et al, A general primer GP5+/GP6+ mediated PCR-enzyme immunoassay method for rapid detection of 14 high-risk and 6 low-risk human papilomavirus genotypes in cervical scrapings. J. Clin. Microbiology, p. 901-905 (1995).
Cole, et al, "Nucleotide Sequence and Comparative Analysis of the Human Papillomavirus Type 18 Genome," Journal of Molecular Biology , vol 193 ( No. 4), p. 599-608 (1987).
Ventana EZ Prep concentrate product sheet. 1113012003.
European Search Report, Jun. 2003.
Schiffman et al., "Accuracy and interlaboratory reliability of human papillomavirus DNA testing by hybrid culture." J. Clin. Microbiol., p. 545-550 (1995).
Seedorf et al., "Human papilomavirus type 16 DNA sequence." Virology, 145:181-185 (1985).
Kennedy et al., "Human papillomavirus type 16 (HPV16), complete genome", NCBI Genbank database, Accession No. K02718 (1985).
Hirt et al., "Nucleotide sequence of human papillomavirus (HPV) type 41: an unusual HPV Type without a typical E2 binding site consensus sequence." Virus Research, p. 179-189 (1991).
Jacobs et al, "Group-specific differentiation between high and low-risk human papillomavirus." J. Clin. Microbiol., p. 901-905, (1997).
Herrington et al., "Interphase cytogenetics using biotin and dioxigenin labelled probes I: relative sensitivity of both molecules for detection of HPV16 in CaSki cells." J. Clin. Pathol. 42:592-600 (1989).

* cited by examiner

*Primary Examiner*—Juliet C Switzer
(74) *Attorney, Agent, or Firm*—McDonnell Boehnen Hulbert & Berghoff LLP

(57) ABSTRACT

Methods and reagents for detecting high-risk human papilloma virus (HPV) DNA types in cells on a Pap smear that indicates the patient is at higher risk for cancer are described. The method uses full-length DNA probes to HPV types 16, 18, 31, 33, 35, and 51 in a particular proportion to hybridize to and detect the viral DNA in situ. The method differentiates high-risk from low-risk HPV DNA in cells that indicates the patient's risk for cancer. The in situ hybridization is detected by brightfield microscopy.

10 Claims, 5 Drawing Sheets

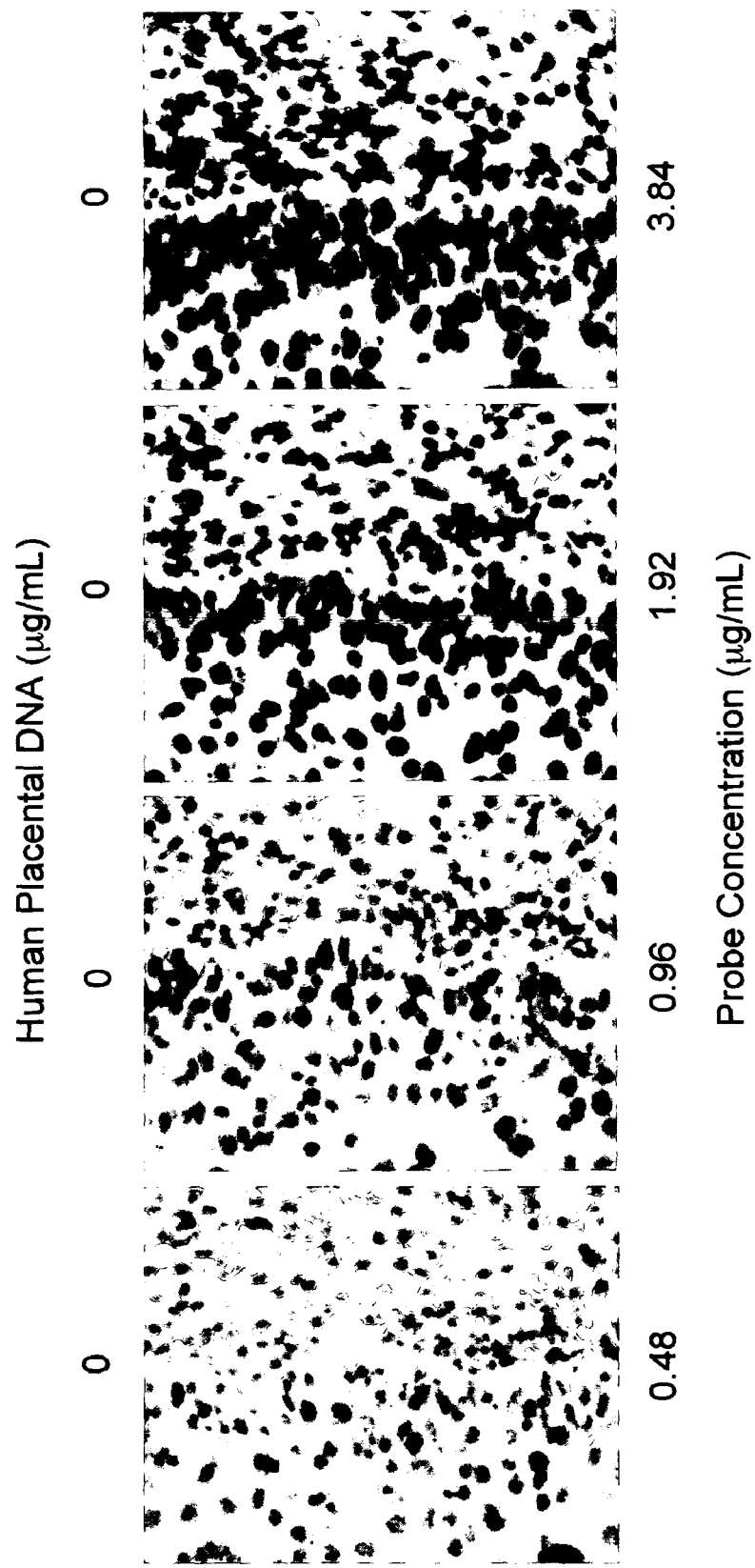

FIG. 3A
FIG. 3B
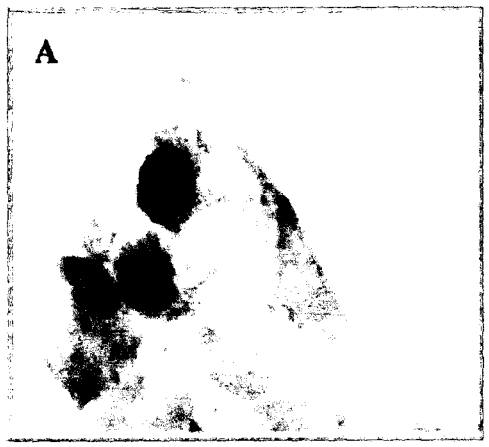
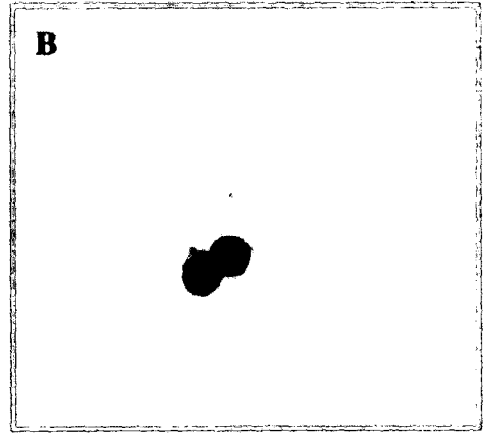

DETECTION OF HUMAN PAPILLOMA VIRUS IN PAPANICOLAOU (PAP) SMEARS

This application is a continuation-in-part of U.S. application Ser. No. 09/582,492, filed Mar. 6, 2002; which claims the benefit of priority of International Application No. PCT/US99/25109, filed Oct. 26, 1999, which was published under PCT Article 21(2) in English; which claims the benefit of priority of U.S. Provisional Application No. 60/105,657, filed Oct. 26, 1998; the disclosure of each of which is explicitly incorporated by reference herein.

BACKGROUND OF THE INVENTION

1. Field of the Invention

The present invention relates to methods and reagents to detect viral DNA in atypical Pap smears indicative of predisposition for cancer.

2. Background of the Invention

Human papilloma virus (HPV) is one of the most common sexually transmitted viral diseases, being manifested in over one million people per year in the United States, and the primary etiologic agent for cervical cancer in women worldwide. There are more than 100 distinct types of HPV, of which approximately 50 are found in the lower genital tract. Of the HPV types found in genital lesions, about 15-20 have been implicated in cervical precancers and cancers. The HPV viral types associated with cervical cancer can be ranked as high-risk, intermediate-risk, or low-risk, according to the tendency of infected individuals to progress to cancer. Common high-risk types include: 16, 18, 39, 45, and 56; intermediate-risk types include: 31, 33, 35, 51, 52, and 58; and low-risk types include: 6, 11, 42, 43, and 44.

HPV is a DNA virus having a genome of about 7900 base pairs in length that contains seven open reading frames that encode five proteins that are expressed early in infection and two that are expressed late in infection. Proteins E6 and E7 are linked to the induction of transformation of benign cells in vitro and in vivo. While the exact mechanism has not yet been established, one of the proteins from high-risk strains appears to inactivate the human tumor suppressor gene p53.

Traditionally, the Papanicolaou (Pap) smear assay has been used to screen individuals for HPV-associated cervical lesions, with Pap smears being performed on women annually to check for the presence of atypical or cancerous cells. Roughly 90% of all smears are normal, 3% are unequivocally dysplastic including LSIL (low-grade squamous intraepithelial lesion), and 7% are squamous atypias (ASC-US; atypical cells of uncertain significance). Patients with a diagnosis of dysplasia are brought back to their doctor's office for biopsy and further procedures. The ASC-US and LSIL diagnoses present the doctor and patient with multiple choices for treatment. If these patients could be tested for the presence of low-risk and high-risk HPV types, such information would greatly aid in determining an optimal course of treatment. For example, the presence of a low-risk HPV type could indicate that no further action—except perhaps for more frequent Pap smears—was required. On the other hand, the presence of a high-risk HPV type could indicate the need for a more aggressive approach, including a cone biopsy, loop electrode excision procedure (LEEP), or ablative therapy (laser surgery or cryotherapy).

An alternative to standard Pap smears is the ThinPrep® Pap test (Cytyc Corp.). A standard Pap smear involves sampling the uterine cervix with a spatula or cytobrush and smearing the cells directly onto a glass slide. The ThinPrep® Pap test involves suspending the sample in a buffered fixative solution which provides better sample recovery, fewer artifacts, multiple slides from one sample, less cell crowding, overlap, and better cellular morphology. In a ThinPrep® Pap test sample, the sampling device is rinsed into a buffered preservative solution and this solution is used to make slides. By suspending the sample in preservative solution and using the ThinPrep® machine to make the slides, the resulting slide is a thin-layer preparation that is clearer of blood, inflammatory cells, mucus, and other obscuring artifacts than a standard Pap smear. The FDA has found the ThinPrep® Pap test to be preferable to the standard Pap smear for the detection of LSIL and more severe lesions. Another advantage of the ThinPrep® Pap test is that the entire sample is not used to make a single slide, and therefore, preserved cells from the unused portion of the sample can be used to make additional slides for the purpose of performing HPV testing.

Both of the standard methods for detecting cervical cancer (i.e., the Pap smear and ThinPrep® Pap test) can be used to detect atypical or cancerous cells, but not HPV infection. Pap smears are classified as: normal; ASC-US (atypical cells of uncertain significance); LSIL (low-grade squamous intraepithelial lesion); or HSIL (high-grade squamous intraepithelial lesion). Currently, about 4.4 million Pap smears are classified as ASC-US and 2.5 million Pap smears are classified as LSIL, annually. This indicates that 6.9 million or 7-8% of all Pap smears per year are ambiguous in their results. Knowledge of the particular HPV type present would aid the patient and clinician in determining the level of risk and treatment options.

Patients with an ambiguous cytology may still have preinvasive or microinvasive cancer and HPV DNA typing may aid in differentiating patients. Studies have shown that ambiguous cytology and high-risk HPV infection with types 16, 18, and 31 are more likely to have high grade SIL or microinvasive histopathology on biopsy. Studies have also suggested that acute infection with HPV types 16 and 18 confer an 11 to 16.9 fold risk of rapid development of cervical intraepithelial neoplasia (CIN).

Accordingly, a need exists to differentiate the borderline Pap smears and ThinPrep® Pap tests based on the HPV type present, if any. Other attempts at preparing oligonucleotide probes have been reported. See U.S. Pat. Nos. 4,820,530; 4,849,311; 4,849,332; 4,849,334; 4,908,306; 4,983,728; 5,057,411; 5,411,847; 5,484,699; 5,501,947; 5,527,898; 5,554,538; and 5,679,509; European Patent No. 0 477 972 B1; and Cole et al., 1987, *J. Mol. Biol.* 193:599-608. Applicants are also aware of U.S. Pat. No. 5,538,871. However, each oligonucleotide probe appears to be specific to only one HPV type and, therefore, numerous probes would be needed to form a complete set capable of detecting all high-risk HPV types.

All patents and references cited herein are explicitly incorporated by reference in their entirety.

SUMMARY OF THE INVENTION

In one aspect, the invention relates to a method for detecting HPV infection by high-risk or low-risk HPV types in individual cells by in situ hybridization.

In a related aspect, the invention relates to a reagent comprising a plurality of full-length genomic probes to certain high-risk HPV types or a second reagent comprising a plurality of full-length genomic probes to certain low-risk HPV types.

In a related aspect, the invention relates to exploiting the cross-reactivity of the probes according to the present invention to determine whether an HPV infected cell has any HPV type that is associated with malignancy, and not only those HPV types completely complementary to the probes.

In another aspect, the invention relates to methods for correlating HPV type detection with conventional cytology characterization as a second factor to determine whether the cells are normal or abnormal.

The present invention achieves these results by using a set of six essentially full-length genomic probes in certain proportions, which under low stringency cross-react with all thirteen currently known high-risk HPV types and none of the low-risk HPV types.

The probes are labeled so that the labeling system may be visualized using conventional light microscopy, which can also separately or simultaneously determine cell morphology as a measure of potential neoplasia. Alternatively, one may use a fluorescent labeling system and fluorescence microscopy to detect the results.

BRIEF DESCRIPTION OF THE DRAWINGS

FIGS. 2A-2B show the results of in situ hybridization HPV analysis using a human placental DNA blocker to reduce probe non-specific binding;

FIGS. 3A-3B show the results of in situ hybridization HPV analysis of a ThinPrep® Pap smear using the INFORM® high-risk assay;

DETAILED DESCRIPTION OF THE INVENTION

Figure 1A:
FIGS. 1A-1B show the results of INFORM®HPV high-risk in situ hybridization analysis using (A) a fluorescein-labeled probe and Amplifier A&B, and (B) a DNP-labeled probe with Amplifier A.

The protocol of the present invention was developed on Pap smears and ThinPrep® samples. This system may also be applied to tissue sections. The samples may be previously stained or embedded in paraffin provided that they are destained or deparaffinized before use. Deparaffination may be performed using heat and detergent or solvent (e.g., xylene).

The probes being used are essentially full-length genomic HPV probes specific for HPV types 16, 18, 31, 33, 35, and 51. The full-length probes of the present invention have essentially the same sequence as given in GenBank® Accession Nos. K02718 (type 16); X05015 (type 18); J04353 (type 31); M62877 (type 51); M12732 and A12360 (type 33); and M74117 (type 35). While some sequence variations and shortening of the probe length are permitted, these are still considered full-length and are not similar to oligonucleotide probes used in the prior art.

These probes range from roughly 6000 to 8000 base pairs each and are mixed together forming a reagent that is a hybridization cocktail for use with a low stringency hybridization solution under low stringency hybridization conditions, and with a lower stringency post-wash solution under lower stringency post-wash conditions. This permits one to detect the thirteen known high-risk HPV types. The probe cocktail was tested on samples of known HPV types to ensure that it was capable of detecting all high-risk types with no cross hybridization to the low-risk types. The results of these experiments, which are provided herein, show a very good signal and low to no background.

The probes are labeled with digoxigenin, fluorescein, or dinitrophenol (DNP) by nick translation; however, a very wide variety of other labeling techniques may be used. Examples include, incorporation during PCR and random priming. The probes need not be labeled at all if one uses an anti-duplex or anti-thymidine dimers antibody.

The in situ hybridization and detection according to the present invention has several advantages over other methods. First, since the present invention is an in situ hybridization, the cytology of the individual cell can be correlated with HPV positive or negative results. Second, since amplification of DNA by PCR, hybrid capture, or other amplification techniques is not needed, the system is less subject to contamination or background yielding false positive or negative results. Third, the processed slides can be stored for years for later reference or confirmation. Fourth, since the reaction is performed on currently used patient sampling methods, no changes need to be instituted at the clinician level. A corollary to this advantage is that the reaction can be performed on destained Pap smears, so the patient does not need to return to the clinician's office for a second sampling in the event of an ambiguous Pap smear cytology. Fifth, the manipulation of the current probe set allows detection of currently classified and unclassified high-risk HPV types. Alternatively, if a Thin-Prep® tube sampling was performed, the same cell suspension can be used to create a slide for the in situ reaction. This allows the extra advantage that the system does not need reformulation to include newly identified HPV types. Sixth, one can differentiate between a few highly positive cells and many weakly positive ones to differentiate between a clinically important or subclinical infection, though ASC-US may be clinically important for reasons other than HPV.

The sample slide is processed through a series of steps to allow target DNA on the sample to hybridize to the probe without losing the morphology of the cell (see method of International Publication No. WO 94/09022 and U.S. patent application Ser. No. 08/272,315, filed Jul. 22, 1994). This includes a Proteinase K digestion and subsequent wash and dehydration steps. The digoxigenin labeled probe and the target DNA are co-denatured for 5 minutes at 95° C. on a hot plate and then hybridization is allowed to proceed for three hours to overnight at 37° C. Following a post-hybridization wash, the slide is incubated with horseradish peroxidase (HRP) conjugated anti-digoxigenin antibody for 30 minutes at 37° C. The detection scheme utilizes the TrueBlue peroxidase substrate (KP Labs, Gaithersburg, Md.). Alternatively, an anti-digoxigenin antibody labeled with alkaline phosphatase with NBT/BCIP as chromogen was also used.

A thirty-minute incubation of the TrueBlue substrate with the HRP detected probe produces a dark blue precipitate at the hybridization site. The cells were then counterstained with eosin, a pink cytoplasmic stain that contrasts well with the TrueBlue reaction product. The results are visualized using brightfield microscopy and can either be imaged or photographed. The slides can be stored indefinitely without losing signal. Elapsed time to set up the slide for hybridization is roughly 35 minutes and the post-hybridization elapsed time before the slide can be visualized is about 65 minutes.

Alternatively, the entire reaction or any part or parts thereof can be run on an instrument such as the Ventana Discovery®. The system can be programmed to perform all the processing steps including deparaffinization, protease digestion, denaturation, hybridization, post-hybridization washing, and any and all antibody or detection steps, up to and including the colorimetric reaction and counterstaining along with all necessary wash and dehydration steps. This has many obvious advantages, including but not limited to increased reproducibility, minimal hands-on time required to run the usually labor-intensive in situ protocol, control of timed steps, and control of reagents.

Alternatively, one may use an automated protease digestion and subsequent wash steps. The probe and target DNA are co-denatured for 5 minutes at 90° C. on a hot plate and then hybridization is allowed to proceed for one hour to overnight at 37° C. Following a post-hybridization wash, the slide is incubated with alkaline phosphatase conjugated anti-digoxigenin antibody for 30 minutes at 37° C. The detection scheme utilizes an alkaline phosphatase substrate NBT/BCIP (Ventana Blue, Gaithersburg, Md.). Alternatively, anti-fluorescein antibody labeled or subsequently conjugated with horseradish peroxidase with TMB as chromogen or alkaline phosphatase with NBT/BCIP as chromogen may also be used.

A thirty-minute incubation of the Ventana Blue substrate with the alkaline phosphatase detected probe produces a blue/black precipitate at the hybridization site. The cells were then counterstained with eosin, a pink cytoplasmic stain that contrasts well with the NBT/BCIP reaction product. The results are visualized using brightfield microscopy and can either be imaged or photographed. The slides can be stored indefinitely without losing signal. Elapsed time to set up the slide for hybridization is roughly 25 minutes and the post-hybridization elapsed time before the slide can be visualized is about 90 minutes. Other detection schemes involving different primary and secondary antibodies and detection reactions based on these or other probe labels can be used with good results.

Brightfield detection is preferable to fluorescence because more laboratories have the necessary equipment, personnel are more familiar with the equipment and observation of cell morphology under brightfield detection, the analysis is easily automated and slides are readily preserved without signal loss. Other labeling systems, e.g., fluorescence, are also acceptable.

The advantages of brightfield detection over fluorescent detection are important in this application. These slides could be preserved without signal loss due to fading, analysis could be more easily automated, and the morphology of the infected or negative cells could be seen by the cytopathologists and cytotechnicians performing the test.

With a positive high-risk HPV in situ result, the clinician may recommend another test every six months and may suggest a minor surgical treatment such as LEEP, but is most likely to recommend colposcopy, probably with a biopsy.

The probes and reagents of the present invention are preferably packaged in kit form containing the probes mixed together as a single reagent in a container. Other reagents for sample treatment, hybridization and wash solutions, label detection systems, and developing reagents for the label detection systems may also be incorporated in one or more other containers.

The following examples are included for purposes of illustrating certain aspects of the invention and should not be construed as limiting.

EXAMPLE 1

Probe Synthesis and Abilities

Six separate plasmids were prepared, one for each HPV type, with one plasmid containing the whole genome of a HPV type and the six types being types 16, 18, 31, 33, 35, and 51. HPV genomes were cloned into plasmids using standard molecular biology techniques that are within the skill of one of ordinary skill in the art. These plasmids were labeled by nick translation with digoxigenin dCTP. The labeled plasmids were then mixed together to form a single reagent. Incorporation of the digoxigenin nucleotide into the labeled DNA was verified by a dot-blot procedure.

The ability of each probe to cross-react with other high-risk HPV types known to be associated with malignancy and not to cross-react with low-risk HPV types not associated with malignancy was tested. The data is given below in Table 1 where the probes used are listed as rows and the Pap smears have the HPV strain listed in the columns. The probe to type 70 was not needed since all high-risk HPV types are covered by other probes. Thus, it was not actually used in the reagent of the present invention.

Since some undesired cross-reactivity was noted with probes to HPV type 16 and 31, the concentration of these two was lowered in the probe reagent to compensate. The percentages of each genomic probe in the DNA cocktail are given in Table 2.

The resulting data was compared against 57 patient samples and resulted in the data of Table 3 where cross-reacting to the low-risk types was essentially nullified. Comparison was made to another commercial HPV probe product.

As shown above, the present probe cocktail was shown to not give false positives with low-risk HPV types unlike the probes of a competitor. Thus, the present invention will give a lower false positive reaction.

Furthermore, when both probe sets were applied to normal Pap smears containing HPV, the Digene probes indicated a positive reaction whereas the cocktail of the present invention did not yield a strong positive reaction. This is an important check as occasionally, Pap smears are misread. It is generally thought that ten percent or more of the population is infected with HPV but this only poses a risk in the presence of dysplasia or other morphological abnormality. Again, the present invention yields fewer false positives.

EXAMPLE 2

Sample Preparation and Pretreatment

Uterine cervix cells were sampled and smeared to form a conventional Pap smear or suspended in PreservCyt® (Cytyc Corp.), a buffered fixative and preservative solution. The ThinPrep 2000 (Cytyc Corp.) was used to make two ThinPrep® slides for each patient. One slide was stained for conventional cytology similar to that of conventional Pap smears and the other slide was prepared as below.

A variety of protease treatments were attempted. The effect of varying the concentrations of proteinase K and pepsin on the intensity of the in situ hybridization signal with an Alu probe on archival, destained Pap smears is given in Table 4. Archived Pap smears were deparaffinized by submersion in xylene and washed in ethanol. Destaining was accomplished by washing the slides for 20 minutes at room temperature in 70% ethanol and 0.1 N HCl. The slides were then washed in tap water for 10 minutes, rinsed in 100% ethanol for 5 minutes, and air-dried. All samples were digested for 20 minutes at 37° C. The post hybridization wash was done at high stringency (60° C., 0.2×SSC, and 2% BSA). The following procedure was used on patient samples.

The Pap smear and the ThinPrep® slide were incubated for 20 minutes at 37° C. in a solution of 10 micrograms per milliliter of Proteinase K in 2×SSC. Following the incubation, the slide was washed for 2 minutes at room temperature in 2×SSC, dehydrated in a series of 70%, 80%, and 95% room temperature ethanol solutions for 1 minute each and air dried.

EXAMPLE 3

Probe and Target Hybridization

A probe solution was made consisting of 0.5 nanograms per milliliter of HPV types 18, 33, 35, and 51 and 0.2 nanograms per milliliter of HPV types 16 and 31 in Hybrisol IX (Ventana) using the probes prepared above. Ten microliters of this probe solution was pipetted onto the sample slide and the specimen was covered with a 22 mm round coverslip and optionally sealed with rubber cement. The slide was placed on a prewarmed 95° C. hot plate for 5 minutes to denature the probe and target DNA and then transferred to a humidified chamber and placed in a 37° C. incubator. The slide was incubated at 37° C. in the humidified chamber for 2 to 16 hours to hybridize. After the 37° C. incubation for hybridization, the rubber cement and coverslip are removed. The slide is washed and the signal detected.

Both high stringency post-hybridization wash conditions (0.2×SSC, 2% BSA, 60° C., 10 minutes) and low stringency post-hybridization wash conditions (2×SSC, 2% BSA, 45° C., 10 minutes) were used on a number of patient samples for which the HPV type was determined. The data is given in Table 5 where detection of different HPV types in cervical biopsies by the high-risk HPV consensus probe as a function of stringency of the post-hybridization wash.

These common HPV types listed comprise about 75% of those types found in lower grade cervical SILs (4-6). Each of the rare HPV types is found in from 1-3% of low grade cervical SILs (4-6). Note that all of the patient samples with high-risk HPV types associated with malignancy were detected under low stringency and none of the low-risk HPV types not associated with malignancy were detected under low stringency.

EXAMPLE 4

Immunochemical Detection

The sample on the slide was then incubated with horseradish peroxidase (HRP) labeled anti-digoxigenin antibody (Boehringer Mannheim GMBH). The slide was washed three times for two minutes each in 1×PBD to remove any unbound or loosely bound antibody. The slide was removed from 1×PBD and allowed to drain briefly. Two hundred microliters of TrueBlue peroxidase substrate was added to the slide and the reaction proceeds at room temperature for three minutes. The slide is rinsed in distilled water and allowed to air dry.

The slide was dipped in a ¼× solution of eosin in ethanol to counterstain. The slide was rinsed three times in distilled water and allowed to air dry. To mount, the slide was dipped in xylenes and a drop of Permount (Fisher) is added. The slide is then covered with a 22 mm round glass coverslip.

Cells with high-risk HPV integrated in the cell demonstrate a blue precipitate in the nuclei with minimal slide background. The cytoplasm is counterstained pink for contrast. Cellular morphology confirms that high-risk HPV types were present in a cell that would be classified as abnormal and normal cells lack any positive signal.

Alternatively, alkaline phosphatase labeled anti-digoxigenin antibody may be used along with NBT/BCIP detection reagents as is used in the attached manuscript.

EXAMPLE 5

Comparison of Pap Smear Results to HPV Type Testing

A sizable number of normal, ASC-US, and SIL Pap smears were tested for HPV type status. Those detected by the probe reagent of the present invention are indicated as positive cases. The detection of HPV DNA using the high-risk consensus probe at low stringency conditions as a function of the cytologic diagnosis and, for cases of ASC-US, clinical follow up data is given in Table 6.

The one normal positive was re-screened by two cytotechnologists who did not know the HPV result and was classified by each as ASC-US. The ASC-US subgrouping was statistically significant difference at p=0.05 using the nonparametric two-tailed Mann-Whitney test as per InStat, Version 2.0 (GraphPad Software, San Diego, Calif.).

EXAMPLE 6

Testing Cell Lines

The probes above were tested against three known cell lines to confirm their ability to detect HPV with respect to the copy number of viruses in each cell line obtained from ATCC. The data is given in Table 7.

EXAMPLE 7

Optimization of In Situ Hybridization HPV Assay

Figure 1B:
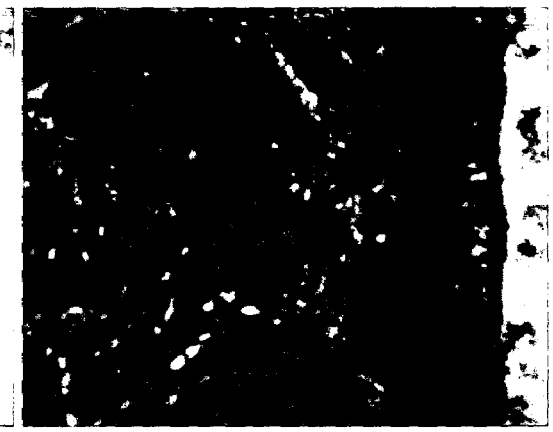
Figure 2B:
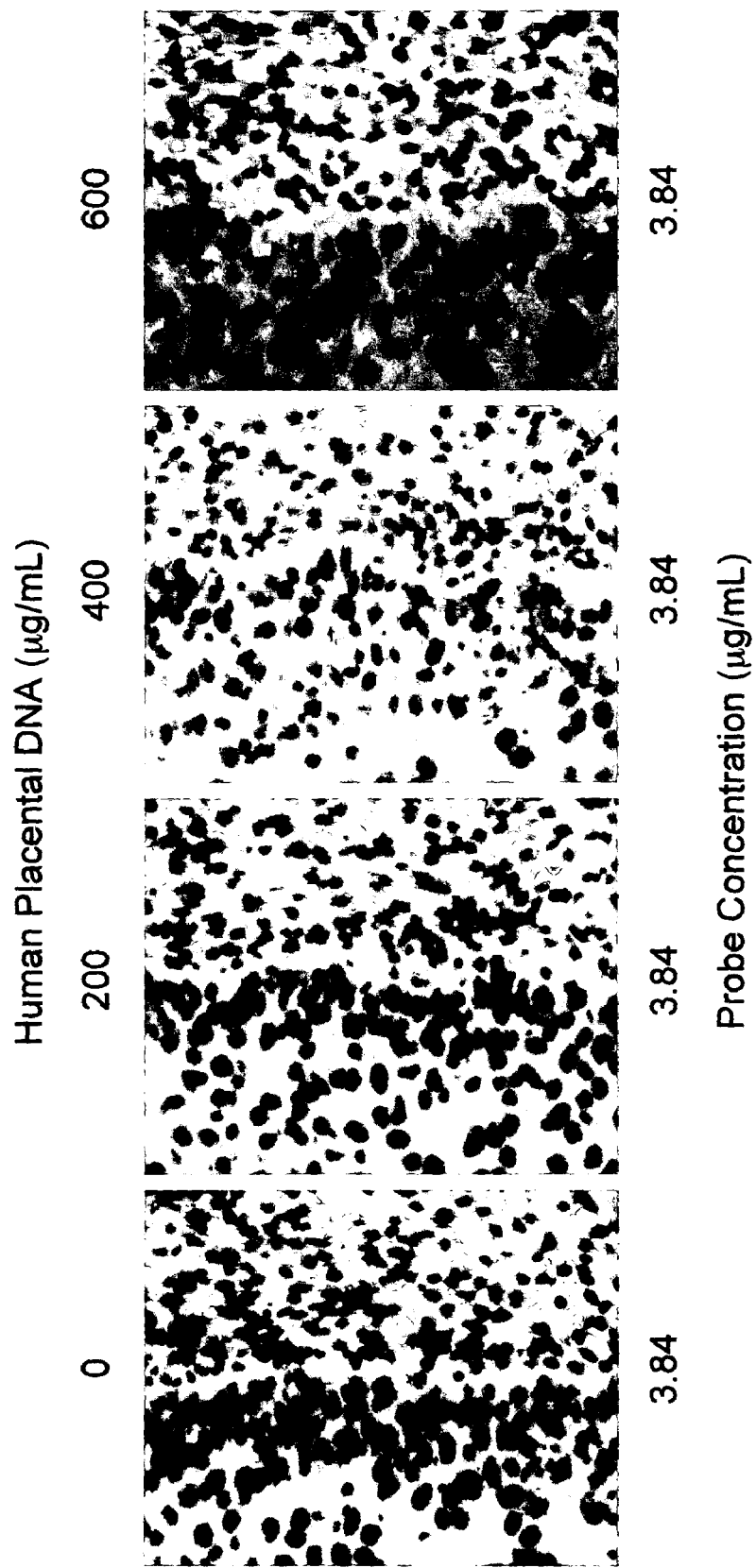

The in situ hybridization HPV assay described herein was optimized by modifying the concentration of probes, adding a signal booster to the reaction mixture, and varying the DNA blocker to be used. Optimal results were obtained using a probe cocktail comprising six high-risk genotypes: 16, 31, 18, 33, 35, and 51, at a ratio of 0.4:0.4:1:1:1:1, and two low-risk genotypes: 6 and 11, at a ratio of 1:1, Amp B as a signal booster, and a human placental DNA blocker. Suitable signal boosters for the in situ hybridization HPV assay described herein include Amp A, a rabbit anti-mouse secondary antibody (Ventana Medical Systems, Inc. catalog #253-2122) and Amp B, a mouse anti-rabbit secondary antibody (Ventana Medical Systems, Inc. catalog #253-2123). The results of INFORM®HPV high-risk in situ hybridization analysis using a fluorescein-labeled probe and Amplifier A&B are shown in FIG. 1A. The results of INFORM®HPV high-risk in situ hybridization analysis using a DNP-labeled probe with Amplifier A are shown in FIG. 1B. FIGS. 2A-2B indicate that a human placental DNA blocker can be used to reduce probe non-specific binding in the in situ hybridization assay described herein.

EXAMPLE 8

Comparison of In Situ Hybridization HPV and Hybrid Capture® II HPV Assays

The efficacy of in situ hybridization (ISH) HPV and Hybrid Capture® (HC) HPV assays was compared by evaluating patients that received an initial cytologic diagnosis of either atypical squamous cells of undetermined significance (ASC-US) or low-grade squamous intraepithelial lesions (LSIL) in ThinPrep® Pap assays (Cytyc, Boxborough, Mass.). All women having ThinPrep® Pap assays performed at the Bayonne Medical Center (Bayonne, N.J.) between December 2001 and July 2002 were included in the study. The cohort of 10,861 women consisted of women aged 17-67 years, with an average age of 36.4 years. Seven hundred sixty-two cases diagnosed as either ASC-US or LSIL on initial cytological screening were examined for HPV determination using the Hybrid Capture® II HPV assay (HCII HPV) (Digene Diagnostics, Inc., Gaithersburg, Md.). These cases were then blinded, and the remainder of the sample was examined by ISH HPV using the INFORM®HPV assay (Ventana Medical Systems, Tucson, Ariz.). Follow-up colposcopic biopsies were received and evaluated on 192 ASC-US and 58 LSIL patients.

HCII HPV testing, which was performed according to the manufacturer's instructions, provided a positive result based on a relative light unit (RLU)/cutoff value ratio of >1.0 with either the high-risk or low-risk probe cocktail. The high-risk cocktail includes eleven full-length RNA probes that recognize thirteen oncogenic HPV types (16, 18, 31, 33, 35, 39, 45, 51, 52, 56, 58, 59, and 68), and the low-risk cocktail includes five probes that recognize the HPV types 6, 11, 42, 43, and 44.

INFORM®HPV testing was performed according to the manufacturer's instructions using the BenchMark® Automated Slide Staining System (Ventana Medical Systems, Tucson, Ariz.). The CaSki cell line, which is positive for oncogenic HPV, and known positive nononcogenic pooled patient specimens were used as controls for each staining run. The probe cocktails demonstrate positive hybridization to thirteen high-risk genotypes (16, 18, 31, 33, 35, 45, 51, 52, 56, 58, 59, 68, and 70) and five low-risk genotypes (6, 11, 40, 42, 43, and 44).

All cases were coded prior to performing INFORM®HPV testing. During the evaluation of ISH slides, no information regarding the patient, Pap assay, HCII HPV assay, or biopsy result was provided to the investigators. ISH slides were initially screened by licensed cytotechnologists at the Bayonne Medical Center, who marked slides for subsequent examination by at least two of four investigating pathologists. Pathologists scored the marked slides for probe reactivity, background, cellular integrity, and cellular adequacy.

In ISH HPV testing, any cells showing a nuclear-specific signal were scored as positive. Two patterns of nuclear staining were observed: (a) a light blue nuclear signal displaying a punctate pattern ranging from single to multiple stipplings (FIG. 3A), which represents HPV DNA integrated into the host DNA, and (b) a generally diffuse and intense nuclear staining pattern (FIG. 3B), which representing HPV DNA in a non-integrated, episomal form. Slides with adequate cellularity and integrity were interpreted as either positive or negative, based on the staining pattern. Slides with positive staining of abnormal cells, regardless of the cellular adequacy or integrity, were interpreted as positive. Slides for four of 254 cases were interpreted as negative, but were removed from the study as falling below the acceptable level for cellular adequacy and integrity, leaving a total of 250 patients. In all but two of these 250 cases, investigating pathologists reached consensus as to a diagnosis. In the two discordant cases (two pathologists reported the samples as indeterminate and two reported them as negative), the slides were scored as negative following subsequent review and discussion by the pathologists.

All cases with a histologic diagnosis of squamous atypia or cervical intraepithelial neoplasia (CIN I, II, or III) were reexamined by all four pathologists, who were blinded to all other results at the time of biopsy evaluation. Pathologists examined at least three tissue levels for each specimen. The World Health Organization (WHO) classification was used to classify cases into different grades of CIN.

HPV DNA results were independently evaluated and compared to the histologic diagnoses of the cervical biopsy for their ability to accurately predict the presence or absence of CIN. The diagnostic accuracy was evaluated against histologic diagnosis by use of common metrics: sensitivity (the proportion of patients identified as positive who are truly positive—the true positive rate), specificity (the proportion of patients identified as negative who are truly negative—the true negative rate), positive predictive value (PPV; the proportion of patients who become positive among those predicted to be positive), and negative predictive value (NPV; the proportion of patients who become negative among those predicted to be negative).

Table 8 indicates that the ISH HPV and HCII HPV assays yielded significantly different results in both the ASC-US and LSIL patient cohorts as to the accuracy of predicting biopsy outcomes. While the positive predictive value (PPV) and negative predictive value (NPV) of the ISH HPV assay was 48% and 99%, respectively, the PPV and NPV of the HCII HPV assay was only 19% and 95%, respectively. The ISH HPV assay scored significantly better with regard to specificity and PPV (P<0.0001). In addition, the false-positive rate for the ISH HPV assay (12%) was significantly lower than the false-positive rate for the HCII HPV assay (39%), and the false-negative rate for the ISH HPV assay (0.4%) was also lower than false-negative rate for the HCII HPV assay (1.6%).

The overall concordance between the two assays was 65% (163/250). In the 87 discordant cases, the ISH HPV assay yielded a positive result in eleven cases in which the HCII HPV assay yielded a negative result, and the HCII HPV assay yielded a positive result in 76 cases in which the ISH HPV assay yielded a negative result. While six of the eleven ISH HPV$^+$/HCII HPV$^-$ cases were confirmed to be positive by biopsy, only one case of the 76 HCII HPV$^+$/ISH HPV$^-$ were identified as positive by biopsy.

Table 9 shows that the ISH HPV assay also outperformed the HCII HPV assay with regard to sensitivity, specificity, PPV, and NPV when the cases were sorted by initial cytologic diagnosis (i.e., ASC-US or LSIL). For the 192 patients diagnosed as ASC-US, the ISH HPV assay produced better results with regard to sensitivity (91% vs. 64%), specificity (91% vs. 62%), PPV (37% vs. 9%), and NPV (99% vs. 97%), and had a lower false-positive rate (8.8% vs. 35.9%) and slightly lower false-negative rate (0.5% vs. 2.1%) than the HCII HPV assay. Similarly, for the 58 patients diagnosed as LSIL, the ISH HPV assay produced better results with regard to sensitivity (100% vs. 89%), specificity (68% vs. 28%), PPV (58% vs. 36%), and NPV (100% vs. 85%), and had a lower false-positive rate (22% vs. 50%) and lower false-negative rate (0.0% vs. 3.4%) than the HCII HPV assay.

Figure 4:
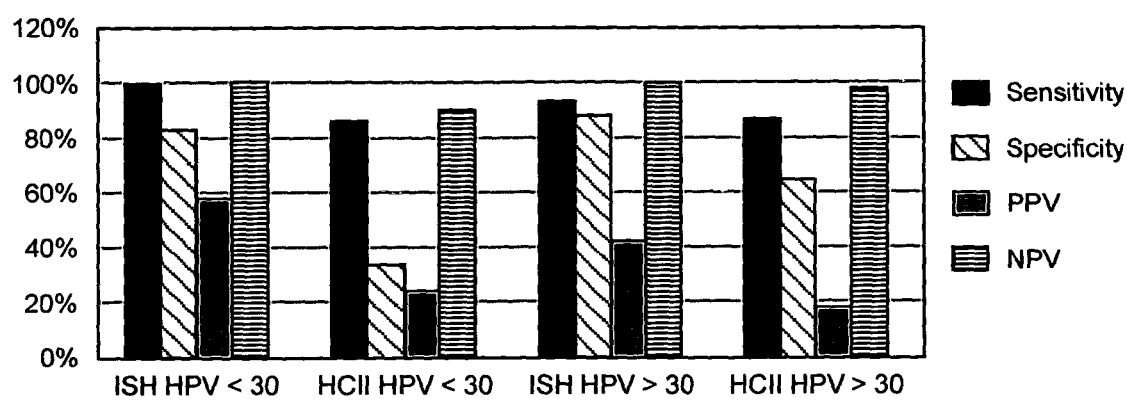
FIG. 4 shows the results of a comparison of the in situ hybridization HPV and Hybrid Capture® II HPV assays in patients younger than 30 years of age (<30) and in patients older than 30 years of age (>30).

FIG. 4 shows that the ISH HPV assay also outperformed the HCII HPV assay with regard to sensitivity, specificity, PPV, and NPV when the cases were sorted by age (i.e., women younger and older than 30 years of age). For both the 72 patients that were younger than age 30 and the 178 patients older than age 30, the ISH HPV assay produced better results with regard to sensitivity, specificity, PPV, and NPV than the HCII HPV assay.

Table 10 shows the results of the ISH HPV and HCII HPV assays in terms of high-risk and low-risk reactivity as correlated with biopsy outcome data. This analysis demonstrates that when only high-risk viral types are used, positive cases may be missed. However, no low-risk$^+$ and CIN II/CIN III$^+$ were identified using either assay, and only one case was identified that is both high-risk$^+$ and low-risk$^+$ positive using the HCII HPV assay.

The results of this comparison indicate that the ISH HPV assay shows increased sensitivity over HCII HPV along with the ability to correlate DNA results with cellular and nuclear morphology (FIGS. 3A-3B). Moreover, the ISH HPV assay does not appear to sacrifice specificity for sensitivity. It is clear that the ISH HPV assay is at least equivalent, if not superior, to the HCII HPV assay with regard to NPV, without sacrificing PPV or specificity (Table 9). In addition, the ISH HPV assay was almost three times more accurate than the HCII HPV assay in predicting colposcopic outcome (Table 9). The HCII HPV assay, in addition to demonstrating lower specificity, sensitivity, PPV, and NPV than the ISH HPV assay, also poorly identified women under age 30 with positive histologic findings (FIG. 4). Furthermore, there appears to be value in evaluating patients for both high-risk and low-risk viral types, as shown in Table 10, as this combined approach increases the sensitivity of both assays. In summary, these results indicate that the ISH HPV assay is a more accurate diagnostic test than the HC HPV assay for predicting histologically demonstrable cervical lesions in women diagnosed with ASC-US and LSIL cytology.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

TABLE 1

|    | 6/11 | 16  | 18 | 31 | 33  | 35  | 39 | 41  | 42  | 43  | 44 | 45  | 51  | 52  | 56  | 58 | 59 | 68 | 70 |
|----|------|-----|----|----|-----|-----|----|-----|-----|-----|----|-----|-----|-----|-----|----|----|----|----|
| 16 | 2    | X   | 0  | 1  | ½   | ½   | 0  | 0   | 1   | ½   | 1  | 0   | ½   | 0   | 0   | 1  | 0  | 0  | 0  |
| 18 | 0    | 0   | X  | 0  | 0   | 0   | 1  | ½   | 0   | 0   | 0  | 2   | 0   | 0   | ½   | 0  | 1  | 1  | 1  |
| 31 | 1    | 1   | 0  | X  | 1   | 2   | 0  | 0   | ½   | 0   | 0  | 0   | 1   | 0   | 1   | 1  | 0  | 0  | 0  |
| 33 | 0    | ½   | 0  | 1  | X   | ½   | 0  | 0   | 0   | 0   | 0  | ½   | 0   | 1   | 0   | 2  | 0  | 0  | 0  |
| 35 | ½    | ½   | 0  | 1  | ½   | X   | 0  | 0   | 0   | 0   | 0  | 0   | 0   | 2   | ½   | ½  | 0  | 0  | 0  |
| 51 | 0    | ½   | 0  | 1  | 0   | 0   | 0  | 0   | 0   | 0   | 0  | 0   | X   | 0   | 0   | 0  | 0  | 0  | 0  |

0 = No Detection
½ = Barely Detected
1 = Light Blue
2 = Moderate Blue
3(X) = Dark Blue

TABLE 2

| HPV 16 | HPV 18 | HPV 31 | HPV 33 | HPV 35 | HPV 51 |
|--------|--------|--------|--------|--------|--------|
| 8.3%   | 20.8%  | 8.3%   | 20.8%  | 20.8%  | 20.8%  |

TABLE 3

| HPV type | Digene Probe | Present Probe Cocktail |
|----------|--------------|------------------------|
| 2        | 3+           | 0                      |
| 6/11     | 1+           | 0                      |
| 6/11     | 1+           | 0                      |
| 6/11     | 2+           | 0                      |
| 6/11     | 3+           | 0                      |
| 6/11     | 3+           | 1+                     |
| 6/11     | 3+           | 0                      |
| 6/11     | 3+           | 0                      |
| 6/11     | 3+           | 0                      |
| 6/11     | 3+           | 0                      |
| 6/11     | 1+           | 0                      |
| 6/11     | 1+           | 0                      |
| 42       | 2+           | 0                      |
| 43       | 2+           | 0                      |
| 44       | 2+           | 0                      |
| 16       | 1+           | 1+                     |
| 16       | 1+           | 1+                     |
| 16       | 2+           | 2+                     |
| 16       | Weak         | 1+                     |
| 16       | 3+           | 3+                     |
| 16       | 3+           | 3+                     |
| 18       | 3+           | 3+                     |
| 31       | 2+           | 2+                     |
| 31       | 3+           | 3+                     |
| 31       | 3+           | 3+                     |
| 33       | 3+           | 3+                     |
| 33       | 2+           | 2+                     |
| 25       | 3+           | 3+                     |
| 35       | 1+           | —                      |
| 51       | 3+           | 3+                     |
| 30       | 3+           | 3+                     |
| 30       | 3+           | 3+                     |
| 30       | 3            | 3+                     |
| 39       | 2            | 1+                     |
| 39       | 2            | 2+                     |
| 39       | 1            | Weak                   |
| 39       | 3            | 3+                     |
| 39       | 3            | 3+                     |
| 39       | 1            | 1+                     |
| 45       | 3            | 3+                     |
| 45       | 3            | 3+                     |
| 52       | 3            | 3+                     |
| 52       | 3            | 3+                     |
| 52       | 2            | 2+                     |
| 56       | 3            | 3+                     |
| 56       | 1            | 1+                     |
| 56       | 3            | 2+                     |
| 56       | 3            | 1+                     |
| 58       | 2            | 1+                     |
| 59       | 2+           | 2+                     |
| 68       | 1+           | 1+                     |
| 70       | 3+           | 3+                     |
| 70       | 2+           | 2+                     |
| 70       | 1+           | 1+                     |
| still novel | 2+        | 2+                     |
| still novel | 1+        | 1+                     |
| still novel | 1+        | 1+                     |

TABLE 4

|  |  | Protease Concentration (µg/mL) | | | | | | | |
|---|---|---|---|---|---|---|---|---|---|
|  |  | 0 | 1 | 10 | 25 | 50 | 100 | 200 | 2,000 |
| Proteinase K | in water | +/− | 1+ | 3+ | 3+ | 3+ | 2+ | 1+ | OD |
|  | in 1X SSC | +/− | 3+ | 1+ | OD | OD | OD | OD | OD |
| Pepsin | in water | +/− | 1+ | 2+ | 2+ | 3+ | 3+ | 2+ | OD |
|  | in 0.1 N HCl | +/− | 0 | 1+ | 1+ | 2+ | 2+ | 3+ | OD |

Signal intensity was scored by the percentage of positive cells (25% = 1+, 25-50% = 2+, >50% = 3+).
OD means overdigested, in which cell morphology is poor and no signal is evident.

TABLE 5

|  |  | HPV DNA Positive | |
|---|---|---|---|
| HPV type |  | Low Stringency[a] | High Stringency[b] |
| Common HPV Types | 6/11 | 0/11 | 0/11 |
|  | 16/18 | 11/11 | 11/11 |
|  | 31/33/35 | 7/7 | 7/7 |
|  | 51 | 4/4 | 4/4 |
| Rare HPV Types | 42/43/44 | 0/3 | 0/3 |
|  | 30 | 3/3 | 1/3 |
|  | 39 | 7/7 | 2/7 |
|  | 45 | 3/3 | 3/3 |
|  | 52 | 3/3 | 1/3 |
|  | 56 | 4/4 | 1/4 |
|  | 58/59/68 | 3/3 | 1/3 |
|  | 70 | 3/3 | 3/3 |

[a]Post-hybridization wash of 10 minutes in 2X SSC with 2% BSA at 45° C.
[b]Post-hybridization wash of 10 minutes in 0.2X SSC with 2% BSA at 60° C.

TABLE 6

| Pap Smear Result | HPV Positive Cases |
|---|---|
| Normal | 1/19 (5%) |
| ASC-US (total) | 16/40 (40%) |
| SIL | 18/23 (78%) |
| ASC-US (biopsy of SIL within 6 months) | 14/21 (67%) |
| ASC-US (biopsy negative for SIL within 6 months) | 2/19 (10%) |

TABLE 7

| Cell Line | HPV Type | Copy Number | Detected |
|---|---|---|---|
| SiHa | 16 | 1 | ✓ |
| HeLa | 18 | 20 | ✓✓ |
| CaSki | 16 | 600 | ✓✓ |

TABLE 8

| HPV Assay Results | Case No.[a] | Positive Biopsy Results[b] |
|---|---|---|
| HCII HPV+ | 121/250 (48%) | 23/121 (19%) |
| HCII HPV− | 129/250 (52%) | 6/129 (5%) |
| ISH HPV+ | 58/250 (23%) | 28/58 (48%) |
| ISH HPV− | 192/250 (77%) | 1/192 (0.05%) |
| HCII HPV+ and ISH HPV− | 76/250 (30%) | 1/76 (1.3%) |
| ISH HPV+ and HCII HPV− | 11/250 (4.4%) | 6/11 (55%) |
| ISH HPV+ and HCII HPV+ | 47/250 (19%) | 23/47 (49%) |
| ISH HPV− and HCII HPV− | 116/250 (46%) | 0 |

[a]Number of patients that are positive or negative for HPV DNA out of the total cohort.
[b]Number of positive biopsy cases as it related to the different result configurations of positive and negative HPV DNA.

TABLE 9

| Diagnosis | Assay | Sensitivity = TP/(TP + FN) (95% CI) | Specificity = TN/(TN + FP) (95% CI) | Positive Predictive Value = TP/(TP + FP) (95% CI) | Negative Predictive Value = TN/(TN + FN) (95% CI) |
|---|---|---|---|---|---|
| ASC-US | ISH HPV | 91% = 10/(10 + 1) (77-99%) | 91% = 164/(164 + 17) (88-94%) | 37% = 10/(10 + 17) (24-59%) | 99% = 164/(164 + 1) (98-100%) |
|  | HC HPV | 64% = 7/(7 + 4) (65-96%) | 62% = 112/(112 + 69) (58-70%) | 9% = 7/(7 + 69) (2-25%) | 97% = 112/(112 + 4) (95-100%) |
| LSIL | ISH HPV | 100% = 18/(18 + 0) (97-97%) | 68% = 27/(27 + 13) (57-79%) | 58% = 18/(18 + 13) (43-71%) | 100% = 27/(27 + 0) (98-98%) |
|  | HC HPV | 89% = 16/(16 + 2) (77-97%) | 28% = 11/(11 + 29) (12-41%) | 36% = 16/(16 + 29) (23-49%) | 85% = 11/(11 + 2) (67-96%) |
| Total | ISH HPV | 97% = 28/(28 + 1) (91-99%) | 86% = 191/(191 + 30) (84-90%) | 48% = 28/(28 + 30) (39-62%) | 99% = 191/(191 + 1) (99-100%) |
|  | HC HPV | 79% = 23/(23 + 6) (77-94%) | 56% = 123/(123 + 98) (52-62%) | 19% = 23/(23 + 98) (14-31%) | 95% = 123/(123 + 6) (94-99%) |

CI = confidence interval;
TP = true positive;
FP = false positive;
FN = false negative;
TN = true negative

TABLE 10

| Assay | High-Risk/Low-Risk Reactivity | Biopsy Negative | CIN I | CIN II/III |
|---|---|---|---|---|
| ISH HPV | high-risk⁻; low-risk⁻ | 191 | 1 | 0 |
| | low-risk⁺ | 5 | 1 | 0 |
| | high-risk⁺ | 19 | 24 | 3 |
| | high-risk⁺; low-risk⁺ | 3 | 2 | 1 |
| | Total | 218 | 28 | 4 |
| HCII HPV | high-risk⁻; low-risk⁻ | 123 | 6 | 0 |
| | low-risk⁺ | 18 | 1 | 0 |
| | high-risk⁺ | 52 | 13 | 1 |
| | high-risk⁺; low-risk⁺ | 29 | 5 | 2 |
| | Total | 222 | 25 | 3 |

What is claimed is:

1. A method for detecting human papilloma virus (HPV) DNA in a cell sample which indicates the patient providing the cell sample is at risk for cancer, comprising:
    (a) adding a reagent comprising a plurality of genomic HPV DNA probe sets to the cell sample under suitable hybridization conditions, wherein:
        (i) a first genomic HPV DNA probe set comprises a plurality of labeled nucleic acid fragments prepared by labeling essentially the full-length genomic sequence of HPV type 16, and which constitute approximately 8.3% of the total HPV DNA in the reagent,
        (ii) a second genomic HPV DNA probe set comprises a plurality of labeled nucleic acid fragments prepared by labeling essentially the full-length genomic sequence of HPV type 18, and which constitute approximately 20.8% of the total HPV DNA in the reagent,
        (iii) a third genomic HPV DNA probe set comprises a plurality of labeled nucleic acid fragments prepared by labeling essentially the full-length genomic sequence of HPV type 31, and which constitute approximately 8.3% of the total HPV DNA in the reagent,
        (iv) a fourth genomic HPV DNA probe set comprises a plurality of labeled nucleic acid fragments prepared by labeling essentially the full-length genomic sequence of HPV type 33, and which constitute approximately 20.8% of the total HPV DNA in the reagent,
        (v) a fifth genomic HPV DNA probe set comprises a plurality of labeled nucleic acid fragments prepared by labeling essentially the full-length genomic sequence of HPV type 35, and which constitute approximately 20.8% of the total HPV DNA in the reagent, and
        (vi) a sixth genomic HPV DNA probe set comprises a plurality of labeled nucleic acid fragments prepared by labeling essentially the full-length genomic sequence of HPV type 51, and which constitute approximately 20.8% of the total HPV DNA in the reagent;

wherein the labeled nucleic acid fragments of the genomic HPV DNA probe sets detectably hybridize to the genomic sequence of HPV types 39, 45, 52, 56, 58, 59, 68 and 70 in addition to detectably hybridizing to the genomic sequence of HPV types 16, 18, 31, 33, 35, and 51; and
    wherein the labeled nucleic acid fragments of the genomic HPV DNA probe sets do not detectably hybridize to the genomic sequence of HPV types 42, 43, or 44; and
    (b) determining whether the labeled nucleic acid fragments of the genomic HPV DNA probe sets detectably hybridize to HPV DNA in the cell sample.

2. The method of claim 1, wherein hybridization conditions comprise washing the cell sample at 45° C. in a buffer comprising 2×SSC and 2% BSA.

3. The method of claim 1, further comprising pretreating the cell sample with a protease.

4. The method of claim 1, further comprising destaining and/or deparaffining the cell sample.

5. The method of claim 1, wherein the cell sample contains abnormal cervical cells.

6. The method of claim 1, wherein the plurality of labeled nucleic acid fragments of the genomic HPV DNA probe sets were labeled by nick translation.

7. The method of claim 1, wherein the plurality of labeled nucleic acid fragments of the genomic HPV DNA probe sets were labeled by polymerase chain reaction (PCR).

8. The method of claim 1, wherein the plurality of labeled nucleic acid fragments of the genomic HPV DNA probe sets were labeled by random priming.

9. A reagent for detecting human papilloma virus (HPV) DNA in a cell sample which indicates the patient providing the cell sample is at risk for cancer, comprising a plurality of genomic HPV DNA probe sets; wherein:
    (a) a first genomic HPV DNA probe set comprises a plurality of labeled nucleic acid fragments prepared by labeling essentially the full-length genomic sequence of HPV type 16, and which constitute approximately 8.3% of the total HPV DNA in the reagent,
    (b) a second genomic HPV DNA probe set comprises a plurality of labeled nucleic acid fragments prepared by labeling essentially the full-length genomic sequence of HPV type 18, and which constitute approximately 20.8% of the total HPV DNA in the reagent,
    (c) a third genomic HPV DNA probe set comprises a plurality of labeled nucleic acid fragments prepared by labeling essentially the full-length genomic sequence of HPV type 31, and which constitute approximately 8.3% of the total HPV DNA in the reagent,
    (d) a fourth genomic HPV DNA probe set comprises a plurality of labeled nucleic acid fragments prepared by labeling essentially the full-length genomic sequence of HPV type 33, and which constitute approximately 20.8% of the total HPV DNA in the reagent,
    (e) a fifth genomic HPV DNA probe set comprises a plurality of labeled nucleic acid fragments prepared by labeling essentially the full-length genomic sequence of HPV type 35, and which constitute approximately 20.8% of the total HPV DNA in the reagent, and
    (f) a sixth genomic HPV DNA probe set comprises a plurality of labeled nucleic acid fragments prepared by labeling essentially the full-length genomic sequence of HPV type 51, and which constitute approximately 20.8% of the total HPV DNA in the reagent;

wherein the labeled nucleic acid fragments of the genomic HPV DNA probe sets detectably hybridize to the genomic sequence of HPV types 39, 45, 52, 56, 58, 59, 68 and 70 in addition to detectably hybridizing to the genomic sequence of HPV types 16, 18, 31, 33, 35, and 51;

and wherein the labeled nucleic acid fragments of the genomic HPV DNA probe sets do not detectably hybridize to the genomic sequence of HPV types 42, 43, or 44.

10. A kit for detecting human papilloma virus DNA in a sample comprising a container containing the reagent of claim 9.

* * * * *